United States Patent [19]
Matta et al.

[11] Patent Number: 5,438,124
[45] Date of Patent: Aug. 1, 1995

[54] GLYCOSYLATING REAGENT FOR THE SYNTHESIS OF LINEAR AND OTHER α-L-FUCOSYL OLIGOSACCHARIDES

[75] Inventors: Khushi L. Matta, Williamsville; Rakesh K. Jain, Amherst; Robert D. Locke, Buffalo, all of N.Y.

[73] Assignee: Health Research, Inc., Buffalo, N.Y.

[21] Appl. No.: 730,662

[22] Filed: Jul. 16, 1991

[51] Int. Cl.$^6$ .............. C07G 3/00; C07H 15/00; C07H 15/24
[52] U.S. Cl. .............. 536/4.1; 536/18.1; 536/123; 536/6.2
[58] Field of Search ............. 536/4.1, 6.2, 18.1, 536/123, 14, 301; 435/14, 301; 546/242; 514/25

[56] References Cited
U.S. PATENT DOCUMENTS

| | | | |
|---|---|---|---|
| 4,277,561 | 7/1981 | Monget et al. | 435/14 |
| 4,563,445 | 1/1986 | Feizi et al. | 536/4.1 |
| 4,652,637 | 3/1987 | Hagmann et al. | 536/6.2 |
| 4,725,557 | 2/1988 | Miyauchi et al. | 536/123 |
| 4,868,110 | 9/1989 | DesRosier et al. | 435/301 |
| 4,956,477 | 9/1990 | Bronstein et al. | 536/18.1 |
| 5,017,704 | 5/1991 | Fleet et al. | 546/242 |

OTHER PUBLICATIONS
Hakomori, S. et al., J. Biol. Chem., 259:4672–4680 (1984).
Fukushi, Y. et al., J. Biol. Chem. 259:4681–4685 (1984).

*Primary Examiner*—David A. Redding
*Assistant Examiner*—Louise N. Leary
*Attorney, Agent, or Firm*—Michael L. Dunn

[57] ABSTRACT

A novel, efficient glycosylating reagent, R 3,4-O-isopropylidene-2-O-(4-methoxybenzyl)-1-thio-β-L-fucopyranoside wherein R is a lower alkyl or lower alkenyl of 1 to 8 carbons such as methyl or pentenyl, is described. This novel reagent provides for the facile synthesis of linear and other α-L-fucosyl oligosaccharides. In addition, a method for the preparation of 2'-O-α-L-fucopyranosyl-lactose, which comprises reacting the abovementioned glycosylating reagent with solvated 4-O-(6-O-acetyl-3,4-O-isopropylidene-β-D-galactopyranosyl)-2,3,5,6-di-O-isopropylidene-D-glucose, dimethyl acetal, a tetrabutylammonium halide and a catalyst and then de-O-acetylating the resulting reaction product with sodium methoxide methanol, is also disclosed.

6 Claims, 1 Drawing Sheet

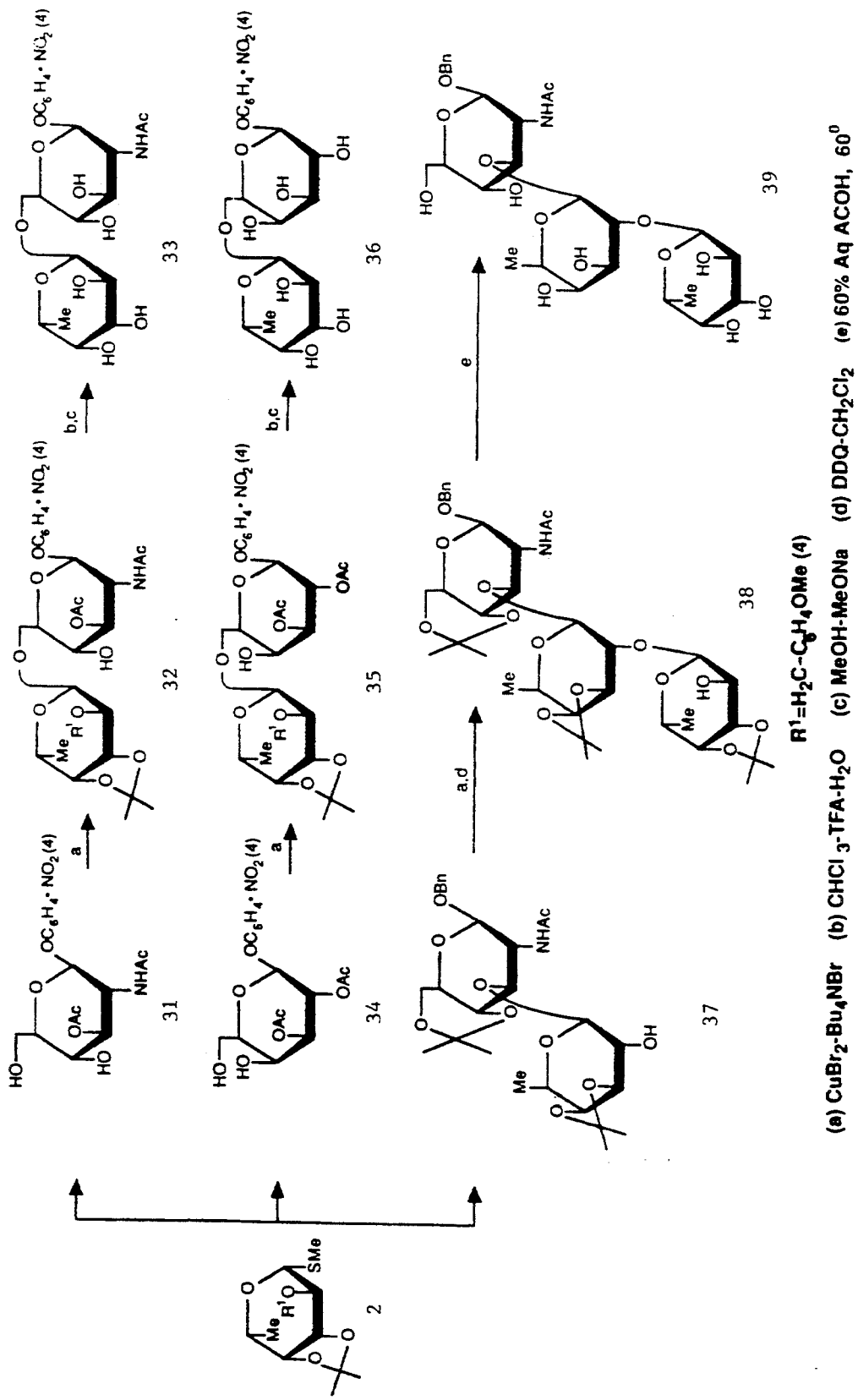

GLYCOSYLATING REAGENT FOR THE SYNTHESIS OF LINEAR AND OTHER α-L-FUCOSYL OLIGOSACCHARIDES

The invention described herein was made in the course of work done under the support of Grant No. CA35329 awarded by the National Cancer Institute, Grant No. DMB87-15954 awarded by the National Science Foundation, and by Grant No. CH 419 awarded by The American Cancer Society.

FIELD OF THE INVENTION

This invention relates generally to the synthesis of linear and other α-L-fucosyl oligosaccharides. More specifically, this invention relates to a novel, efficient glycosylating reagent for the synthesis of linear and other α-L-fucosyl oligosaccharides containing the Fucα1–3GlcNAcβ- sequence linked to the C-6 position. More particularly, this invention relates to the synthesis of linear L-fucosyl oligosaccharides containing α-L-(1→2) interglycosidic linkages utilizing the above-mentioned glycosylating reagent.

BACKGROUND OF THE INVENTION

A variety of tumor-associated glycoproteins and glycolipids carrying X determinant [Galβ1→4(Fucα]→3)GlcNAc] and sialylated X determinant structures have been reported. Some of these glycoconjugates contain repetitive 3-fucosyllactosamine (X determinant) units. For example, the fucolipid, Galβ1→4(Fucα1→3)GlcNAcβ1→3Galβ1→4(Fucα1→3)GlcNAcβ1→4Galβ1→4Glcβ1→Cer, has been isolated from human colonic and liver adenocarcinoma by Hakomori and co-workers. These investigators have recommended the need for isolation of hybridoma producing a monoclonal antibody which should specifically recognize the internal fucosyl sequence, Fucα1→3GlcNAcβ1→3Galβ1→4(Fucα1→3)GlcNAcβ1→3Gal, and not the external X determinant, because, such an antibody would be unique in detecting structures specific for human cancer. A closer look at many of these tumor associated fucosyl glycoconjugates reveals that the X determinant is attached at either the C-6 position of D-GalNAc, D-Man and D-Gal; the C-2 of D-Man or the C-3 position of D-Gal.

It is well known in the art that the use of a hexopyranosyl glycosyl donor having a "nonparticipating" group at the O-2 position has resulted in high yields of α-linked oligosaccharides. For α-L-fucosylation of an appropriately protected acceptor, glucosylating reagents such as: methyl 1-thio-2,3,4-tri-O-benzyl-β-L-fucopyranoside, 2,3,4-tri-O-benzyl-β-L-fucopyranosyl fluoride; 2,3,4-tri-O-benzyl-α/β-L-fucopyranosyl trichloroacetimidate and 2,3,4-tri-O-benzyl-α-L-fucopyranosyl bromide, under halide ion catalyzed conditions have been used.

When the synthesis of α-L-fucopyranosyl oligosaccharides are desired, the literature has focused upon methyl 1-thio-2,3,4-tri-O-benzyl-β-L-fucopyranoside, 2,3,4-tri-O-benzyl-β-L-fucopyranosyl fluoride, and 2,3,4-tri-O-benzyl-α/β-L-fucopyranosyl trichloroacetamide as the glycosylating agents of choice. Each of the above glycosylating reagents employ O-benzyl protection which necessitates hydrogenolysis for removal.

BRIEF DESCRIPTION OF THE INVENTION

The invention concerns the novel compound R-3,4-O-isopropylidene-2-O-(4-methoxybenzyl)-1-thio-β-L-fucopyranoside wherein R is a lower alkyl or lower alkenyl of 1 to 8 carbon atoms, such as methyl or pentenyl. This novel compound is useful in that it can provide for the facile synthesis of linear and other α-L-fucosyl oligisaccharides by acting as a powerful glycosylating reagent. These compounds are desirable for biomedical research in that they can be used as synthetic or artificial antigens, as well as other important uses. In addition, the invention herein disclosed is particularly suited to synthesizing nitrophenyl oligisaccharides containing the α-L-Fuc(1–3) β-D-GlcNAc unit at their non-reducing end, as well as fucosyl oligosaccharides containing an anomeric p-nitrophenyl or benzyl group and oligosaccharides containing the Fuc1–3Glc NAcβ- sequence linked to the C-6 position of different sugars.

Further, a method for the preparation of 2'-O-α-L-fucopyranosyl-lactose is described which comprises reacting the compound of the invention with solvated 4-O-(6-O-acetyl-3,4-O-isopropylidene-β-D-galactopyranosyl)-2,3,5,6-di-O-isopropylidene-D-glucose, dimethyl acetal, a tetrabutylammonium halide and a catalyst and then de-O-acetylating the resulting reaction product with sodium methoxide methanol.

This novel glycosylating reagent not only eliminates the need for O-benzyl protection, but also provides for the efficient, convenient, rapid and economical synthesis of the abovementioned compounds.

Hence, it is an objective of the current invention to provide a rapid method of synthesis for producing oligosaccharides that possess a 4-nitrophenyl group at their reducing end.

It is a further objective of the current invention to provide a more efficient route for α-L-fucosylation.

It is a still further objective of the current invention to provide a straight forward method for protecting group removal eliminating the need for hydrogenolysis.

It is an objective of the current invention to provide a facile approach toward the synthesis of linear L-fucosyloligosaccharides containing α-L-(1→2) interglycosidic linkages.

It is a still further objective of the current invention to provide a method for the facile and stereoselective synthesis of fucosyl oligosaccharides containing an anomeric p-nitrophenyl or benzyl group.

It is yet another objective of the current invention to provide a convenient and rapid method for the synthesis of 2'-O-α-L-fucopyranosyl.

It is still another objective of the current invention to provide a facile method of synthesizing nitrophenyl oligosaccharides containing the α-L-Fuc (1→3) β-D-GlcNAc unit at their nonreducing end.

It is still another objective of the current invention to provide a facile method of synthesizing oligosaccharides containing the Fucα1→3GlcNAcβ→ sequence linked to the C-6 position of different sugars.

BRIEF DESCRIPTION OF THE DRAWING

The drawing illustrates certain applications of the invention in the convenient synthesis of several oligosaccharides containing an anomeric p-nitrophenyl or benzyl group.

DETAILED DESCRIPTION OF THE INVENTION

The invention herein involves synthesis of oligosaccharides containing the Fucα1→3GlcNAcβ→ sequence linked to the C-6 position of different sugars, to utilize selected glycoconjugate fragments in immunological studies. The named invention facilitates the rapid efficient syntheses of 4-nitrophenyl 2-acetamido-2-deoxyy-3-O-α-L-fucopyranosyl-β-D-glycopyranoside, 2-nitrophenyl O-(α-L-fucopyranosyl)-(1-3)-O-(2-acetamido-2-deoxy-β-D-glucopyranosyl)(1-6)-2-acetamido-2-deoxy-β-D-galactopyranoside, 4-nitrophenyl O-(α-L-fucopyranosyl)-(1-3)-O-(2-deoxy-β-D-glucopyranosyl)-(1-6)-α-D-mannopyranoside, and 4-nitrophenyl O-(α-L-fucopyranosyl)-(1-3)-O-(2-acetomido-2-deoxy-β-D- glucopyranosyl)-(1-6)-β-D-galctopyranoside. Such compounds can be employed as synthetic or artificial antigens. Reduction of their nitro groups with subsequent covalent linkage to bovine serum albumin (BSA) through a diazotization reaction, provides hapten-carrier conjugates for use as immunogens.

One way in which the current invention may be utilized is the synthesis of oligosaccharides possessing a 4-nitrophenyl group at their reducing end. Selected structures may be used as synthetic or artificial antigens. Desired immunogens may be obtained through reduction of the nitro groups and subsequent coupling of the resulting amino groups to proteins.

In all of the examples herein disclosed, the melting point was determined with a Fisher-Johns apparatus and is uncorrected. Optical rotations were measured at 25° C. with a Perkin-Elmer 241 ™ polarimeter. Thin-layer chromotography (t.l.c.) was conducted on aluminum sheets, precoated with 0.2 mm layers of silica gel 60F-254 (E. Merk, Darmstadt, Germany). The components were located either by exposure to u.v. light or by spraying with 5% $H_2SO_4$ in ethanol (or both) and charring. Silica gel used for column chromatography was Baker Analyzed ™ (600–200 mesh). $^1$H-n.m.r. spectra were recorded at 25°; $^1$H-n.m.r. spectra with a Varian ™ EM-390, and $^{13}$C-n.m.r. spectra with a Bruker ™ AM-400 instrument, at 90 and 100.6 MHz, respectively; the chemical shifts (δ) are expressed from the tetramethylsilane signal. Solutions in organic solvents were generally dried with anhydrous $Na_2SO_4$. Dichloroethane and N,N-dimethylformamide were dried over 4A° molecular sieves. Elemental analyses for carbon, hydrogen and nitrogen were performed by Robertson Laboratory, 29 Samson Avenue, Madison, N.J. 07940, U.S.A.

Preparation of Methyl 3,4-O-Isopropylidene-2-O-(4-methoxybenzyl)-1-Thio-β-L-Fucopyranoside(2)

To a stirred solution of methyl 3,4-O-isopropylidene-1-thio-β-L-fucopyranoside (1) (2.0 g) in N,N-dimethylformamide (20 ml) was added sodium hydride (0.7 g) portionwise, and the stirring continued for 0.5 h at room temperature. The mixture was then cooled (0°, bath), 4-methoxybenzyl chloride (1.8 ml) was added, and stirring continued for 2 h at room temperature. After careful addition of methanol to decompose excess NaH, solvent was evaporated and the residue dissolved in chloroform. This solution was washed with water, dried, and concentrated under diminished pressure. The residue was applied to a column of silica gel and eluted with 10% ethyl acetate in hexane to give a 79% yield of a product having properties consistent with (Compound 2) above, $[α]_D$ −1.1° (c 1.4, chloroform): $^1$H-n.m.r. (CDCl$_3$): δ7.33 (d, J 9 Hz, 2 H, arom.), 7.17 (d, J 9 Hz, arom.), 3.43 (s, 3 H, OMe), 2.15 (s, 3 H, SMe), 1.52–1.35 (cluster of singlets, 9 H, CMe).

Anal. Calc. for $C_{17}H_{24}O_5S$: C, 59.97; H, 7.11. Found: C, 59.81; H, 7.32.

Synthesis of Nitrophenyl Oligosaccharides Containing the α-L-Fuc(1-3) β-D-GlcNAc Unit at Their Non-Reducing End Utilizing Methyl 3,4-O-Isopropylidene-2-O-(4-methoxybenzyl)-1-Thio-β-L-Fucopyranoside

Example A

A solution of 4-nitrophenyl 2-acetamido-2-deoxy-4,6-O-isopropylidene (0.75 g, 1.96 mmol) and Compound 2 above (0.9 g, 2.54 mmol) in 5:1 dichloroethane-N,N-dimethylformamide (60 ml) was stirred for 0.5 h with 4A° molecular sieves (5 g) under protection from light and moisture. Tetrabutylammonium bromide (1.3 g, 4.03 mmol) and CuBr$_2$ (0.94 g, 4.03 mmol) were added, and the mixture stirred for 16 h at room temperature. The reaction mixture was filtered through Celite ™, the solids were thoroughly washed with chloroform, and the filtrate and washings combined and then washed with aq. NaHCO$_3$, and then water, dried, and concentrated under diminished pressure. The residue was applied to a column of silica gel and eluted with 5% acetone in chloroform. On concentration, the fractions gave 1.3 g at 95% yield of a product having properties consistent with the above structure of 4-nitrophenyl 2-acetamido-2-deoxy-3-O-(3,4-O-isopropylidene-4-methoxybenzyl-α-L-fucopyranosyl)-4,6-O-isopropylidene-β-D-glucopyranoside (3). (1.3 g, 95%), as an amorphous solid, $[α]_D$ −57.6° (c 0.7, chloroform); $^1$H-n.m.r. (CDCl$_3$): δ8.13 (d, J 9 Hz, 2 H, arom.), 7.30–6.77 (m, 6 H, arom.), 3.77 (s, 3 H, OMe), 1.64 (s, 3 H, NAc) , 1.46–1.23 (cluster of singlets, 15 H, CMe).

Anal. Calc. for $C_{34}H_{44}N_2O_{13}$: C, 59.29; H, 6.44; N, 4.07. Found: C, 59.56; H, 6.37; N, 3.85.

Example B

To a solution of Compound 3 above (0.5 g) in chloroform (50 ml), trifluoroacetic acid (5.0 ml) water (0.5 ml) were added. After stirring for 2 h at room temperature, the solution was evaporated to dryness. Residual acid was removed by several co-evaporation with toluene. The residue was purified in a column of silica gel with 20% methanol in chloroform as the eluant to afford 4-nitrophenyl 2-acetamido-2-deoxy-3-O-α-L-fucopyranosyl-β-D-glucopyranoside (4) (0.25 g, 71%) as a solid, $[α]_D$ −77.4° (c 0.3, methanol); for $^{13}$C-n.m.r. data see Table I.

Anal. Calc. for $C_{20}H_{28}N_2O_{12}H_2O$: C, 47.43; H, 5.97; N, 5.53. Found: C, 47.49; H, 5.89; N, 5.73.

Example C

To a stirred solution of 2-nitrophenyl 2-acetamido-2-deoxy-6-O-(2-acetamido-2-deoxy-β-D-glucopyranosyl)-α-D-galactopyranoside (5, 0.6 g) in N,N-dimethylformamide (30 ml) were added 4-toluenesulfonic acid monohydrate (0.05 g) and 2,2-dimethoxypropane (5 ml). Stirring was continued for 3 h at 70° C. after which the acid was neutralized by addition of triethylamine, and the solvent evaporated in vacuo. The residue was dissolved in acetone, filtered and addition of ether-hexane afforded 2-nitrophenyl 2-acetamido-2-deoxy-6-O-(2-acetamido-2-deoxy-4,6-O-isopropylidene-$\beta$-D-glucopyranosyl)-3,4-O-isopropylidene-$\alpha$-D-galactopyranoside (6) (0.6 g; 87.2%) as an amorphous solid; $[\alpha]_D$ +87° (c0.6, methanol); 1H-n.m.r. (CDCl$_3$+ DMSO (d$_6$): $\delta$7.90–7.40 (m, 4 H, arom.), 1.92 and 1.86 (each s, 3 H, NAc), 1.50–1.32 (cluster of singlets, 12 H, CMe).

Anal. Calc. for C$_{20}$H$_{39}$N$_3$O$_{13}$: C, 53.75; H, 6.28; N, 6.72. Found: C, 53.63; H, 5.99; N, 6.95.

Example D

Compound 6 above (0.165 g; 0.26 mmol) was treated with thiomethyl donor 2 (0.12 g, 0.34 mmol) in 5:1 dichloroethane-N,N-dimethylformamide (12 ml) in the presence of tetrabutylammonium bromide (0.165 g; 0.51 mmol) and CuBr$_2$(0.12 g, 0.51 mmol), and 4A° molecular sieves (1 g) in a manner analogous to that described for the preparation of compound 3. After the aforedescribed processing, the crude reaction product was applied to a column of silica gel and eluted with 2% methanol in chloroform. On concentration, the fractions corresponding to 2-nitrophenyl O-(3,4-O-isopropylidene-2-O-4-methoxybenzyl-$\alpha$-L-fucopyranosyl)-(1→3)-O-(2-acetamido-2-deoxy-4,6-O-isopropylidene-$\beta$-D-glucopyranosyl)-(1→6)-2-acetamido-2-deoxy-3,4-O-isopropylidene-$\alpha$-D-galactopyranoside (7) (0.23 g, 93.7%) gave an amorphous solid, $[\alpha]_D$ −23° (c 0.8, chloroform); 1H-n.m.r. (CDCl$_3$): $\delta$7.82 (d, J 9 Hz, 1 H, arom.). 7.65–7.13 (m, 5 H, arom.), 6.82 (d, J 9 Hz, 2 H, arom.), 5.38 (d, J 3 Hz, 1 H, H-1″), 3.77 (s, 3 H, OMe), 1.70 (s, 3 H, NAc), 1.53 (s, 3 H, NAc), 1.38–1.16 (cluster of singlets, 21 H, CMe).

Anal. Calc. for C$_{45}$H$_{61}$N$_3$O$_{18}$: C, 57.99; H, 6.60; N, 4.51. Found: C, 58.04; H, 6.54; N, 4.29.

Example E

A solution of Compound 7 above (0.1 g) in chloroform (30 ml) was treated with trifluoroacetic acid (1.5 ml) and water (0.3 ml) for 2 hr at room temperature. After processing as described for Compound (3) (to give (Compound 4)), residue was dissolved in methanol. Addition of ether precipitated 2-nitrophenyl O-$\alpha$-L-fucopyranosyl-(1→3)-O-(2-acetamido-2-deoxy-$\beta$-D-glucopyranosyl)-(1→6)-2-acetamido-2-deoxy-$\alpha$-D-galactopyranoside (8) (0.055 g, 74.3%), $[\alpha]_D$ −23.9° (c 0.63, water); for 13C-n.m.r. data, see Table I.

Anal. Calc. for C$_{28}$H$_{41}$N$_3$O$_{17}$.H$_2$O: C, 47.39; H, 6.11; N, 5.92. Found: C, 47.49; H, 5.89; N, 5.73.

Example F

A solution of 4-nitrophenyl 2,3-O-isopropylidene-6-O-(2-acetamido-3,4,6-tri-O-acetyl-2-deoxy-$\beta$-D-glucopyranosyl)-$\alpha$-D-mannopyranoside (9; 1.4 g) in 0.01M sodium methoxide in methanol (25 ml) was stirred for 3 h at room temperature. The base was neutralized with Amberlite™ IR-120 (H+) cation-exchange resin, the resin suspension was filtered, and the filtrate concentrated to give a solid residue. To a stirred solution of this solid in N,N-dimethylformamide (20 ml) were added 4-toluenesulfonic acid monohydrate (0.06 g) and 2,2-dimethoxypropane (12 ml). Stirring was continued for 16 h at room temperature. The acid was neutralized by addition of a few drops of triethylamine and solvent evaporated. The residue was applied to a column of silica gel and eluted with 10% methanol in chloroform to give 4-nitrophenyl 2,3-O-isopropylidene-6-O-(2-acetamido-2-deoxy-4,6-O-isopropylidene-$\beta$-D-glucopyranosyl)-$\alpha$-D-mannopyranoside (10) (1.1 g, 90.1%), $[\alpha]_D$ +23.3° (c 1.1, methanol); 1H-n.m.r. (CDCl$_3$): $\delta$8.17 (d, J 9 Hz, 2 H, arom.), 7.14 (d, J 9 Hz, 2 H, arom.), 1.95 (s, 3 H, NAc), 1.51–1.37 (cluster of singlets, 12 H, CMe).

Anal. Calc. for C$_{26}$H$_{36}$N$_2$O$_{13}$: C, 53.42; H, 6.21; N, 4.79. Found: C, 53.21; H, 6.49; N, 5.02.

Example G

Compound 10 above (0.46 g, 0.79 mmol) was treated with glycosyl donor Compound 2 (0.37 g, 1 mmol) in 5:1 dichloroethane-N,N-dimethylformamide (42 ml) in the presence of tetrabutylammonium bromide (0.51 g, 1.58 mmol), CuBr$_2$ (0.37 g, 1.58 mmol) and 4A° molecular sieves (4 g) for 16 h at room temperature. After processing as described above for the preparation of Compound 3, t.l.c. showed the presence of two major products, both faster migrating than Compound 10. The crude product was chromatographed and eluted with a solvent gradient consisting of 5–15% acetone in chloroform. The earlier fractions collected contained the faster migrating tetrasaccharide 4-nitrophenyl O-(3,4--O-isopropylidene-2-O-4-methoxybenzyl-$\alpha$-L-fucopyranosyl)-(1→3)-O-(2-acetamido-2-deoxy-4,6-O-isopropylidene-$\beta$-D-glucopyranosyl)-(1→6)-[O-(3,4-O-isopropylidene-2-O-4-methoxybenzyl-$\alpha$-L-fucopyranosyl)-(1→4)]-2,3-O-isopropylidene-$\alpha$-D-mannopyranoside (13). On concentration, the fractions corresponding to Compound 13 (0.25 g, 26.5%) gave an amorphous solid, $[\alpha]_D$ −37.4° (c 0.7, chloroform); 1H-n.m.r. (CDCl$_3$): $\delta$8.15 (d, J 9 Hz, 2 H, arom.), 7.33–6.75 (m, 10 H, arom.), 3.78 (s, 6 H, 2×OMe), 1.55 (s, 3 H, NAc), 1.45–1.15 (cluster of singlets, 30 H, CMe).

Anal. Calc. for C$_{60}$H$_{80}$N$_2$O$_{23}$: C, 60.19; H, 6.74; N, 2.34. Found: C, 60.38; H, 6.69; N, 2.18.

The latter fractions contained pure desired trisaccharide derivative 4-nitrophenyl O-(3,4-O-isopropylidene-2-O-4-methoxybenzyl-$\alpha$-L-fucopyranosyl)-(1→3)-O-(2-acetamido-2-deoxy-4,6-O-isopropylidene-$\beta$-D-glucopyranosyl)-(1→6)-2,3,0-isopropylidene-$\alpha$-D-mannopyranoside (13) (0.3 g, 42.8%), $[\alpha]_D$ +11.8° (c 0.7, chloroform); 1H-n.m.r. (CDCl$_3$): $\delta$8.12 (d, J 9 Hz, 2 H, arom.), 7.23–7.01 (m, 4 H, arom.), 6.75 (d, J 9 Hz, 2 H, arom.), 3.72 (s, 3 H, OMe), 1.51 (s, 3 H, NAc), 1.43–1.19 (cluster of singlets, 21 H, CMe).

Anal. Calc. for C$_{43}$H$_{58}$N$_2$O$_{18}$: C, 57.97; H, 6.56; N, 3.15. Found: C, 58.11; H, 6.53; N, 2.94.

Example H

Compound 11 above (0.15 g) in chloroform was treated with trifluoroacetic acid-water, as described for Compound 3 (to give Compound 4), to afford 4-Nitrophenyl O-$\alpha$-L-fucopyranosyl-(1→3)-O-(2-acetamido-2-deoxy-$\beta$-D-glucopyranosyl)-(1→6)-$\alpha$D-mannopyranoside (12) (0.08 g, 73%), $[\alpha]_D$ −13.9° (c 0.6, water); for 13C-n.m.r. data, see Table I.

Anal. Calc. for C$_{26}$H$_{38}$N$_2$O$_{17}$: C, 47.99; H, 5.89; N, 4.31. Found: C, 47.97; H, 5.85; N, 4.22.

Example I

Compound 13 above (0.2 g) in chlorform (30 ml) was treated with trifluoroacetic acid (1.5 ml) and water (0.3 ml) under stirring for 2 h at room temperature. The mixture was then processed as described for Compound 7 (to give Compound 8) to furnish amorphous 4-nitrophenyl O-$\alpha$-L-fucopyranosyl-(1→3)-O-(2-acetamido-2-deoxy-$\beta$-D-glucopyranosyl)-(1→6)-[O-($\alpha$-

L-fucopyranosyl)-(1→4)]-α-D-mannopyranoside (14) (0.12 g, 90%), [α]$_D$ −34.9° (c 0.5, water).

Anal. Calc. for C$_{32}$H$_{48}$N$_2$O$_{12}$.1.5 H$_2$O: C, 46.65; H, 6.24; N, 3.40. Found: C, 46.88; H, 6.41; N, 3.12.

Example J

A mixture of 4-nitrophenyl-3,4-O-isopropylidene-β-D-galactopyranoside (1.35 g, 3.96 mmol), 2-methyl-(3,4,6-tri-O-acetyl-1,2-dideoxy-α-D-glucopyrano)-[2,1-d]-2-oxazoline (1.6 g, 4.86 mmol), and 4-toluene sulfonic acid monohydrate (0.1 g) in 1,2-dichloroethane (100 ml), protected from moisture, was heated for 16 hr at 70° in an atmosphere of N$_2$. The mixture was cooled, the acid neutralized by the addition of a few drops of pyridine, and the solution concentrated to dryness. Examination of the crude product by t.l.c. in 3:2 (v/v) chloroform-acetone revealed the presence of a major product migrating slower than the starting materials, and also some slower migrating contaminants (presumably decomposition products of oxazoline). The crude material was purified by silica gel column chromatography. Elution with solvent gradient consisting of 10–15% acetone in chloroform furnished 4-nitrophenyl 3,4-O-isopropylidene-6-O-(2-acetamido-3,4,6-tri-O-acetyl-2-deoxy-β-D-glucopyranosyl)-β-D-galactopyranoside (15) (1.1 g, 41.5%), [α]$_D$ −36.2° (c 0.9, chloroform); $^1$H-n.m.r. (CDCl$_3$): δ8.27 (d, J 9 Hz, 2 H, arom.), 7.12 (d, J 9 Hz, 2 H, arom.), 2.07 (s, 3 H, OAc), 2.05 (d, 6 H, 2×OAc), 1.65 (s, 3 H, NAc), 1.52 and 1.33 (each s, 3 H, CMe).

Anal. Calc. for C$_{29}$H$_{38}$N$_2$O$_{16}$: C, 51.94; H, 5.71; N, 4.18. Found: C, 51.83; H, 5.67; N, 4.25.

Example K

Compound 15 above (0.9 g) after O-deacetylation with 0.01 methanolic-sodium methoxide, was treated with 2,2-dimethoxypropane exactly as described for Compound 9 (to give Compound 10). After processing as just described for the preparation of Compound 10, the residue was purified on a column of silica gel with 5% methanol in chloroform as the eluent. Evaporation of the fractions corresponding to 4-nitrophenyl 3,4-O-isopropylidene-6-O-(2-acetamido-2-deoxy-4,6-O-isopropylidene-β-D-glucopyranosyl)-β-D-galactopyranoside (16) (0.7 g, 80.3%) gave an amorphous solid, [α]$_D$ −101.2° (c 0.7, methanol);- $^1$H-n.m.r. (CDCl$_3$+Me$_2$SO$_4$-d$_6$): δ8.19 (d, J 9 Hz, 2 H, arom.), 7.12 (d, J 9 Hz, 2 H, arom.), 1.64 (s, 3 H, NAc), 1.45–1.27 (cluster of singlets, 12 H, CMe); $^{13}$C-n.m.r. data (CD$_3$OD+Me$_2$SO$_4$-d$_6$): δ111.11 (CMe$_2$), 103.30 (C-1'), 101.34 (C-1), 100.76 (CMe$_2$), 74.99 (C-3), 73.53 (C-3' and C-4'), 73.04 (C-2), 69.98 (C-4), 68.62 (C-6), 63.11 (C-6'), 57.93(C-2').

Anal. Calc. for C$_{26}$H$_{36}$N$_2$O$_{13}$: C, 53.42; H, 6.21; N, 4.79. Found: C, 53.63; H, 5.99; N, 4.95.

Example L

A mixture of Compound 16 (0.59 mg, 1 mmol) in dichloromethane (25 ml), 5% aq. sodium hydroxide (2 ml), benzoyl chloride (0.13 ml, 1.1 mmol), and tetrabutylammonium hydrogen sulfate (0.06 g, 0.18 mmol) was stirred for 1 h at room temperature, and the two layers were separated. The organic layer was washed with water, aq. sodium bicarbonate solution, dried, and concentrated to dryness. The residue was applied to a column of silica gel and eluted with 2% methanol in chloroform to give 4-Nitrophenyl 2-O-benzoyl-3,4-O-isopropylidene-6-O-(2-acetamido-2-deoxy-4,6-O-isopropylidene-β-D-glucopyranosyl)-β-D-galactopyranoside (17) (0.6 g, 87.8%), amorphous, [α]$_D$ −42.7° (c 0.8, methanol); $^1$H-n.m.r. (CDCl$_3$): δ8.17–7.91 (m, 5 H, atom.), 7.40 (d, J 9 Hz, 2 H, atom.), 6.95 (d, J 9 Hz, 2 H, arom.), 1.68 (s, 3 H, NAc), 1.59–1.33 (cluster of singlets, 12 H, CMe), $^{13}$C-n.m.r. (CD$_3$OD+Me$_2$SO$_4$-d$_6$): 111.77 (CMe$_2$), 103.41 (C-1'), 100.78 (CMe$_2$), 99.19 (C-1), 75.23 (C-2), 74.32 (C-3), 73.83 (C-3'), 73.04 (C-4'), 69.89 (C-4), 68.65 (C-6), 63.12 (C-6'), 57.89 (C-2').

Anal. Calc. for C$_{33}$H$_{40}$N$_2$O$_{14}$: C, 57.55; H, 5.84; N, 4.07. Found: C, 57.68; H, 5.56; N, 4.22.

Example M

Compound 17 (0.55 g, 0.8 mmol) was treated with thiomethyl 2 (0.38 g, 1.07 mmol) in 5:1 dichloroethane-N,N-dimethylformamide (30 ml) in the presence of tetrabutylammonium bromide (0.52 g, 1.6 mmol) and CuBr$_2$ (0.38 g, 1.6 mmol), and 4A° molecular sieves (3 g) for 16 h at room temperature. After processing as described for the preparation of Compound 3, the crude product mixture was treated with 0.01M sodium methoxide in methanol for 2 hr. The base was neutralized with Amberlite™ IR-120 (H+) cation-exchange resin, the resin suspension was filtered, and the filtrate concentrated to dryness. The residue was purified on a column of silica gel with 5% acetone in chloroform as the eluent. The fractions corresponding to 4-nitrophenyl O-(3,4-O-isopropylidene-2-O-4-methoxybenzyl-α-L-fucopyranosyl)-(1→3)-O-(2-acetamido-2-deoxy-4,6-O-isopropyl-idene-β-D-glucopyranosyl)-(1→6)-3,4-O-isopropylidene-β-D-galactopyranoside (18) were concentrated to give an amorphous solid (0.65 g, 91%), [α]$_D$ −61.9° (c 0.5, chloroform); $^1$H-n.m.r. (CDCl$_3$): δ8.21 (d, J 9 Hz, 2 H, arom.), 7.33–7.03 (m, 4 H, arom.), 6.80 (d, J 9 Hz, 2 H, arom.), 3.75 (s, 3 H, OMe), 1.55–1.22 (cluster of singlets, 24 H, NAc and CMe).

Anal. Calc. for C$_{43}$H$_{58}$N$_2$O$_{18}$: C, 57.97; H, 6.56; N, 3.15. Found: C, 58.04; H, 6.54; N, 3.19.

Example N

A solution of Compound 18 above (0.4 g) in chloroform (75 ml) was treated with trifluoroacetic acid (3 ml) and water (0.3 ml) for 2 h at room temperature. After processing as described for Compound 3 (to give Compound 4), the crude product was purified in a column of silica gel by using chloroform-methanol-water (5:4:1; v/v/v) as the eluent to give 4-nitrophenyl O-α-1-fucopyranosyl-(1→3)-O-(2-acetamido-2-deoxy-β-D-glucopyranosyl)-(1→6)-β-D-galactopyranoside (19) (0.19 g, 65%) amorphous; [α]$_D$ −109.6° (c 0.6, water); for $^{13}$C-n.m.r. data, see Table I.

Anal. Calc. for C$_{26}$H$_{38}$N$_2$O$_{17}$.2H$_2$O: C, 45.47; H, 6.18; N, 4.08. Found: C, 45.32; H, 6.32; N, 4.19.

TABLE I

| PROPOSED $^{13}$C-N.M.R. CHEMICAL SHIFTS[a] | | | | | | | | |
|---|---|---|---|---|---|---|---|---|
| Residue | Compound | C-1 | C-2 | C-3 | C-4 | C-5 | C-6 | CH$_2$CO |
| β-D-GlcNAc—OC$_6$H$_4$NO$_2$ (4) | 4 | 97.86 | 54.34 | 80.86 | 68.46 | 77.02 | 60.31 | 22.89 |
| α-L-Fuc-(1 → 3) | | 99.83 | 68.14 | 69.67 | 71.63 | 66.51 | 16.34 | |
| α-D-GalNAc—OC$_6$H$_4$NO$_2$ (2) | 8 | 99.88 | 49.28 | 73.82 | 70.76 | 74.63 | 69.73 | 24.72 |
| β-D-GlcNAc-(1 → 6) | | 103.82 | 57.84 | 83.40 | 71.41 | 78.70 | 63.63 | 24.92 |
| α-L-Fuc-(1 → 3) | | 102.73 | 70.95 | 71.47 | 72.36 | 70.04 | 17.96 | |

TABLE I-continued

| PROPOSED $^{13}$C-N.M.R. CHEMICAL SHIFTS$^a$ | | | | | | | | |
|---|---|---|---|---|---|---|---|---|
| Residue | Compound | C-1 | C-2 | C-3 | C-4 | C-5 | C-6 | CH$_2$CO |
| α-D-Man-OC$_6$H$_4$NO$_2$ (4) | 12 | 100.58 | 72.42 | 74.68 | 69.79 | 75.35 | 69.52 | |
| β-D-GlcNAc-(1 → 6) | | 103.80 | 57.96 | 83.59 | 71.61 | 78.67 | 63.76 | 25.08 |
| α-L-Fuc-(1 → 3) | | 102.81 | 71.28 | 72.42 | 73.18 | 70.85 | 18.01 | |
| β3-D-Gal-OC$_6$H$_4$NO$_2$ (4) | 19 | 102.75 | 74.64 | 75.09 | 71.39 | 76.77 | 69.78 | |
| β-D-GlcNAc-(1 → 6) | | 103.74 | 57.96 | 83.43 | 71.73 | 78.73 | 63.65 | 24.88 |
| α-L-Fuc-(1 → 3) | | 102.75 | 71.57 | 72.38 | 73.04 | 70.77 | 17.99 | |

$^a$For solutions in D$_2$O with Me$_4$Si as the internal standard.

PRODUCTION OF 2'-O-α-FUCOPYRANOSYL-LACTOSE

Among the many constituents that comprise the complex mixture of biological substances contained in human milk are an abundance of glycosylated oligosaccharides (such as 2'-O-α-L-fucopyranosyl-lactose). Preliminary indications suggest that the presence of these disaccharides is important to the physiological development of the nursing infant. This consideration does not present any significant impact upon artificial formulas presently supplied for nursing full-term infants. Their development apparently proceeds very satisfactorily on formulas which lack high concentrations of human milk-specific components. However, the maturation of low birth weight infants progresses less smoothly and is often beset with a series of complications which seem to result from maturation deficiencies. An understanding of how particular human milk components influence the physiological maturation of specific tissues or organ systems can lead to specific therapeutic uses of these components for ill, undersized or developmentally delayed infants.

The invention herein disclosed allows convenient, economical and ready access to large amounts of pure materials for evaluation and potential development of physiologically important milk components. The current invention promises availability of a wide range of previously difficult to attain structures in addition to 2'-O-α-L-fucopyranosyl-lactose.

Preparation of Pentenyl 3,4-O-Isopropylidene-2-O-(4-methoxybenzyl)-1-Thio-β-L-Fucopyranoside (22)

Condensation of 2,3,4-tri-O-acetyl-α-L-fucopyranosyl bromide with penten-1-ol in the presence of active silver carbonate in dichloromethane gave a crude intermediate which after de-O-acetylation with sodium methoxide-methanol provided pentenyl β-L-fucopyranoside (Compound 20), $[\alpha]_D$ +29.4 (c 1.8, water), in 94.4% yield after silica gel column chromatography. Compound 20 on treatment with 2,2-dimethoxypropane in N,N-dimethylformamide in the presence of 4-toluenesulfonic acid monohydrate gave pentenyl 3,4-O-isopropylidene-β-L-fucopyranoside (21) in 98% yield, $[\alpha]_D$ −23.2 (c 1.8, chloroform); $^1$H-n.m.r. (CDCl$_3$): δ5.97–5.52 (m, $^1$H, =CH), 1.51 and 1.35 (each s, 3H, CMe), 0.87 (d; J 7Hz, CMe). Compound 21 on alkylation with NaH, 4-MeOBnCl in DMF then afforded the desired pentenyl 3,4-O-isopropylidene-2-O-(4-methoxybenzyl)-β-L-fucopyranoside (22) in good yield, $[\alpha]_D$ −45.2 (c 0.7, chloroform): $^1$H-n.m.r. (CDCl$_3$): δ7.30 (d, J 9Hz, 2H, arom), 6.83 (d, J 9Hz, 2H, arom. ), 3.80 (s, 3H, OMe), 1.47–1.28 (m, 6H, CMe) 0.90 (d, J 7Hz, 3H, CMe).

Example O

Preparation of 2'-O-α-L-Fucopyranosyl-Lactose Utilizing Pentenyl 3,4-O-Isopropylidene-2-O-(4-methoxybenzyl)-1-Thio-β-L-Fucopyranoside(22)

A solution of 4-O-(6-O-acetyl-3,4-O-isopropylidene-β-D-galactopyranosyl)-2,3:5,6-di-O-isopropylidene-D-glucose dimethyl acetal (23; 0.55 g, 1 mmol) and Compound 2 (0.6 g, 1.3 mmol) in dichloroethane/N,N-dimethylformamide (36 ml, 5:1 v/v) was stirred in the presence of CuBr$_2$ (0.47 g, 2 mmol), Bu$_4$NBr (0.64g, 2 mmol) and 4Å molecular sieves (4.0 g) for 16 hr. at room temperature. Further amounts of Compound 2 (0.3g, 0.65 mmol) and CuBr$_2$-Bu$_4$NBr (1 mmol each) were added and the stirring continued for another 16 hrs. After being processed in the usual manner, the crude product was de-O-acetylated with sodium methoxide-methanol and purified by silica gel column chromatography (5% acetone in chloroform) to afford Compound 24 in 59.1% yield (on the basis of Compound 23), $[\alpha]_D$ −44.6 (c 0.75, chloroform); $^1$H-n.m.r. (CDCl$_3$): δ7.23 (d, J 9Hz, 2H, arom), 6.75 (d, J 9Hz, 2H, arom), 5.37 (d, J 4Hz, $^1$H, H-1"), 3.77 (s, 3H, OMe), 3.51 (s, 6H, 2×OMe), 1.66–1.18 (cluster of singlets, 27H, CMe). In the $^1$H-n.m.r. spectrum of Compound 24, the resonance for H-1" was observed at δ5.37 (J 4Hz) indicating an a-configuration at the new interglycosidic linkage. The glycosylation of Compound 23 with the donor Compound 22 using iodonium dicollidene perchlorate as a catalyst in ether-dichloromethane resulted in a mixture of α- and β-linked trisaccharides (compounds 24 and 25 in approx. 9:1 ratio as determined by $^1$H-nmr). It is noteworthy that the removal of both protecting groups, 4-methoxybenzyl and isopropylidene, of Compound 24 is achieved in one step by using CHCl$_3$-TFA-H$_2$O. Compound 25 has a specific rotation of −49.5° (initial-)−−51.8° (after 3 days) (c 0.5, water) which corresponds to that reported in the literature.

PRODUCTION OF FUCOIDAN AND OTHER SULFATED OLIGOMERS

Fucoidan is a sulfated polymer of L-fucose which contains repeating subunits of 2-O-α-L-fucopyranoside with sulfate groups located on either C-3 or C-4 positions. Fucoidan and other sulfated oligomers are presently finding increased biochemical application. As a result, a demand now exists for well-defined sulfated oligosaccharides. In order to provide for the efficient synthesis of fucosyl saccharides containing repetitive (α1-2) interglycosidic linkages, a suitable glycosylating reagent capable of incorporating an L-fucose moiety containing a temporary blocking group at the C-2 position, thus allowing facile chain elongation, needed to be found. The novel compound R-3,4-O-isopropylidene-2-O-(4-methoxybenzyl) -1-thio-β-L-fucopyranoside, wherein R is a lower alkyl or lower alkenyl,is an effective glucosylating reagent for this and other useful applications.

Example P

Compound 2 on reaction with methyl 3,4-O-isopropylidene-α-L-fucopyranoside performed in the presence of CuBr2-Bu4NBr in Cl(CH)2Cl-DMF (5:1, v/v for 24h) gave exclusively the α-disaccharide derivative Compound 26 in 72% yield. Selective removal of the methoxybenzyl group in Compound 26 gave a key intermediate alcohol Compound 27 having its C-2' hydroxy free $[\alpha]_D$ −169.16° (c 0.7, CHCl3) in 92% yield. A key glycosylation reaction between Compound 2 and acceptor Compound 27 was performed successfully and stereoselectively under similar conditions to give the desired α-linked trisaccharide protected derivative Compound 28 $[\alpha]^D$ −164.35 (c 0.7, CHCl3) in 66% yield after silica gel column chromatography. Once again selective removal of the p-methoxybenzyl group in Compound 28 proceeded smoothly to give the aglycon hydroxide Compound 29. Deacetonation of Compound 29 with 60% aqueous $CH_3COOH$ at 60° provided the trisaccharide, Fucα1–2Fucα1–2Fucα-OCH3(30). Structural conformation of the final products was accomplished through $^{13}C$-n.m.r. investigation.

It is apparent the the key intermediate alcohol, Compound 29, can be used as a candidate for further glycosylation and elongation of the carbohydrate chain. It is noteworthy that this glycosylating reagent contains 4-methoxybenzyl, a non-participating group at the C-2 position which is easily removed for subsequent incorporation of the α-L-linkage, and its removal does not require hydrogenolysis. As a result, its use is attractive for the synthesis of various other α-L-fucosyl saccharides, especially oligosaccharides containing p-nitrophenyl, azido or allyl functional groups. The drawing illustrates further applications of the invention in the convenient synthesis of several oligosaccharides containing an anomeric p-nitrophenyl or benzyl group. Condensation of 4nitrophenyl 2-acetamido-3-O-acetyl-2-deoxy-β-D-glucopyranoside (31), 4-nitrophenyl 2,3-di-O-acetyl-β-D-galactopyranoside (34) and benzyl 2-acetamido-2-deoxy-3-O-(3,4-O-isopropylidene-β-D-fucopyranosyl)-4–6-O-isopropylidene-β-D-glucopyranoside (37) with this reagent afforded their respective α-linked fucosylated derivatives 32, 35 and 38 in good yields. It is noteworthy that the removal of both the protecting groups, e.g. 4-methoxybenzyl and isopropylidene,is achieved in one step. The $^{13}C$-n.m.r. spectra of the final compounds 33, 36, and 39 were in agreement with the structure assigned. Compound 33 has a specific rotation of −90.8° which corresponds to that reported earlier by the inventors.

Data for compounds in the drawing are given below. As follows: Cmpd. no, yield (%), values of $[\alpha]_D$ measured at 25°±3° for solutions in a. CHCl3 b. CH3OH c. H2O and partial C-13 (δ) in D2O. 32:(85.7), −80.8°(a) 33:(79.8), −90.8°(c); 101.61, 101.26 (C-1', C-1), 70.93 (C-6) 35:(78.5), −94.4°(a) 36:(96.6), −121.5°(b); 102.96, 101.74 (C-1, C-1'), 71.40 (C-6) 38:(60.3), −27.3°(a) 39:(77.9), −72.3°(c); 103.57,102.90, 102.17 (C-1', C-1", C-1), 81.03 (C-3), 78.99 (C-2)

Further modifications of the invention herein disclosed will occur to persons skilled in the art and all such modifications are deemed to be within the scope of the invention as defined by the appended claims.

What is claimed is:

1. The compound R-3,4-O-isopropylidene-2-O-(4-methoxybenzyl)-1-thio-β-L-fucopyranoside wherein R is a lower alkyl or lower alkenyl of 1 to 8 carbon atoms.

2. The compound of claim 1 wherein R is methyl.

3. The compound of claim 1 wherein R is pentenyl.

4. A process for the preparation of 2'-O-α-L-fucopyranosyl-lactose which comprises reacting the compound of claim 1 with solvated 4-O-(6-O-acetyl-3,4-O-isopropylidene-β-D-galactopyranosyl)-2,3,5,6-di-O-isopropylidene-D-glucose, dimethyl acetal, a tetrabutylammonium halide and a catalyst for the reaction and then de-O-acetylating the resulting reaction product with sodium methoxide methanol.

5. The process of claim 4 wherein the tetrabutylammonium halide is tetrabutyl ammonium bromide, the catalyst is cupric bromide and the solution is a mixture of dichloroethane and N,N-dimethylformamide in a 5:1 volume to volume ratio.

6. The process of claim 5 wherein the reaction product is de-O-acetylated with sodium methoxide-methanol and then purified by silica gel column chromatography.

* * * * *